Figure 1:
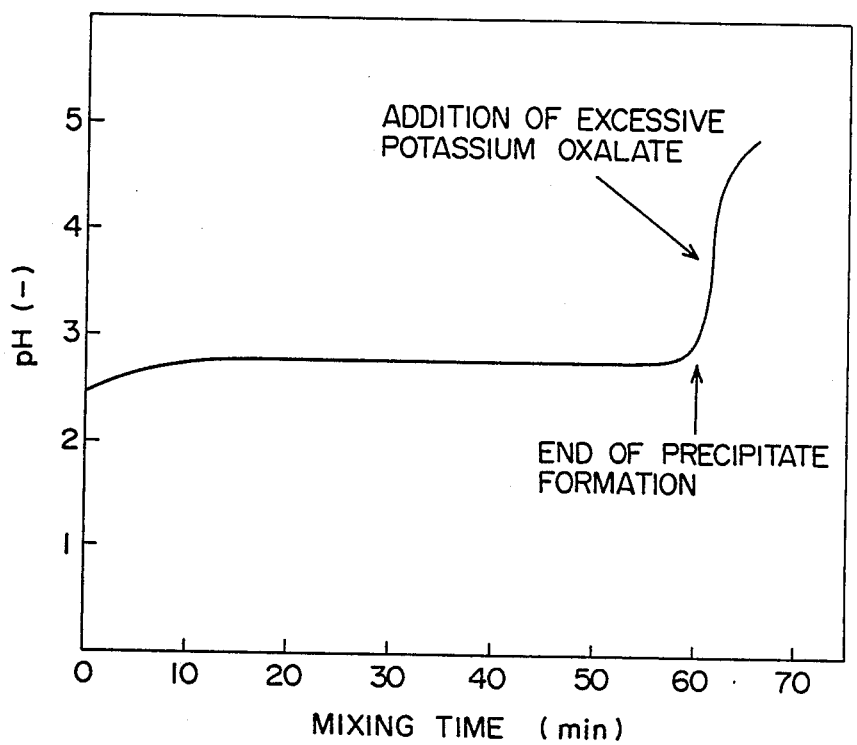

United States Patent [19]

Nojiri et al.

[11] Patent Number: 4,746,749

[45] Date of Patent: May 24, 1988

[54] PROCESS FOR PRODUCING SILVER OXALATE

[75] Inventors: Naohiro Nojiri, Tsuchiura; Yukio Sakai; Tomoatsu Iwakura, both of Ami, all of Japan

[73] Assignee: Mitsubishi Petrochemical Co., Ltd., Tokyo, Japan

[21] Appl. No.: 70,805

[22] Filed: Jul. 7, 1987

[30] Foreign Application Priority Data

Jul. 12, 1986 [JP] Japan .............................. 51-164308

[51] Int. Cl.$^4$ ................................................ C07F 1/10
[52] U.S. Cl. ................................................ 556/114
[58] Field of Search ......................................... 556/114

[56] References Cited

U.S. PATENT DOCUMENTS

| | | | |
|---|---|---|---|
| 2,630,444 | 3/1953 | Fugassi et al. | 556/114 |
| 3,133,942 | 5/1964 | Hahl | 556/114 X |
| 3,458,544 | 7/1969 | Bryan | 556/114 X |
| 4,102,820 | 7/1978 | Cavitt | 252/463 |
| 4,207,210 | 6/1980 | Kilty | 252/463 |

FOREIGN PATENT DOCUMENTS 1,369,639 10/1974 United Kingdom .

OTHER PUBLICATION

MacDonald, J. Chem. Soc. 832–839, Tompkins, Trans. Faraday Soc., 44 206, Finch et al. J. Chem. Soc. 2053, Haynes, Discussions of the Faraday Soc. 31 229. Leiga. J. Phys. Chem., 70 3254

*Primary Examiner*—Paul F. Shaver
*Attorney, Agent, or Firm*—Wenderoth, Lind & Ponack

[57] ABSTRACT

A process for producing silver oxalate, which comprises reacting
(a) one member selected from the group consisting of oxalic acid and oxalic acid salts as one reactant, with
(b) a silver salt as the other reactant, at a pH of not more than 5 in an aqueous medium thereby to precipitate silver oxalate.

11 Claims, 1 Drawing Sheet

PROCESS FOR PRODUCING SILVER OXALATE

This invention relates to a process for producing silver oxalate. More specifically, it relates to a process for producing silver oxalate having a large particle diameter.

As is well known, water-insoluble silver oxalate is produced by adding oxalic acid or a water-soluble oxalate salt to a silver salt such as silver nitrate in aqueous solution.

Silver-supported catalyts are used for the production of ethylene oxide by vapor-phase oxidation of ethylene. Silver oxalate is used as a raw material for the preparation of such silver-supported catalysts.

The specifications of Japanese Patent Publications Nos. 11895/1980 and 1629/1983 and Japanese Laid-Open Patent Publication No. 82691/1977 disclose a process for producing a silver-supported catalyst for production of ethylene oxide by the vapor-phase oxidation of ethylene, which comprises adding oxalic acid and/or a water-soluble oxalate salt to a silver salt such as silver nitrate in aqueous solution to form a precipitate of water-insoluble silver oxalate, collecting the precipitate by filtration, washing it, thereafter adding water and a complexing agent such as an amine to dissolve the silver oxalate precipitate as a silver complex salt, impregnating a porous refractory carrier with the solution, and heat-treating the impregnated carrier to decompose the silver complex salt and deposit silver on the carrier.

Example 1 of the above Japanese Patent Publication No. 1629/1983 describes that 6 g of anhydrous silver nitrate and 3.3 g of potassium oxalate were dissolved separately in 100 ml of water; the solutions were mixed and heated in a steam bath; the precipitate of the resulting silver oxalate was centrifugally separated and the liquid present on the surface was removed by decantation; and the precipitate was further washed five times with 100 ml of hot distilled water at 60° to 90° C., and in the meanwhile, it was centrifuged after every washing, and water was removed by decantation.

As can be understood from the fact that the precipitate of the resulting silver oxalate is separated by centrifugation, a silver oxalate precipitate obtained by simply mixing an aqueous solution of silver nitrate and an aqueous solution of potassium oxalate and heating the mixture as shown above consists of fine particles, has a high water content and is sticky. Because of this, the precipitate has the defect that (1) it has poor settlability, (2) it has poor filtrability in separation by filtration, and the separation requires a special filter or is time-consuming, and (3) much time is required for washing with water. When this precipitate is to be used in the preparation of a catalyst for production of ethylene oxide, it adheres to the filter, the filter cloth, etc. and also to a container for transporting it to the next step of preparing a silver complex salt, and to a device for feeding materials for the preparation of a silver complex. This results in disadvantages in catalyst production, such as a loss of expensive silver and much time and labor involved.

It is an object of this invention therefore to provide a novel process for producing silver oxalate industrially advantageously.

Another object of this invention is to provide a process for producing silver oxalate having excellent settlability, filtrability and water washability.

Still another object of this invention is to provide a process for producing a precipitate of silver oxalate which has a surprisingly large particle size and a low water content and is non-sticky and easy to handle.

Yet another object of this invention is to provide a process for producing silver oxalate which can be very advantageously used in the preparation of a catalyst for oxidation of ethylene to ethylene oxide because a complexing step of dissolving it by reaction with an amine ends more rapidly than in the case of using fine silver oxalate.

Further objects of this invention along with its advantages will become apparent from the following description.

According to this invention, the above objects and advantages of this invention are achieved by a process for producing silver oxalate, which comprises reacting
- (a) one member selected from the group consisting of oxalic acid and oxalic acid salts as one reactant, with
- (b) a silver salt as the other reactant, at a pH of not more than 5 in an aqueous medium thereby to precipitate silver oxalate.

FIG. 1 of the accompanying drawings shows variations of pH in a mixing reaction tank in the production of silver oxalate.

Figure 2:
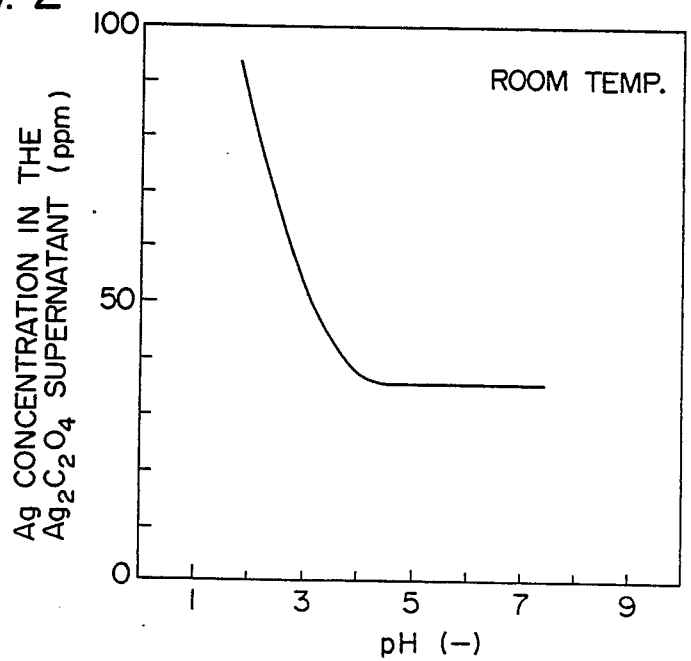

FIG. 2 of the accompanying drawings shows the dependence of the solubility of silver oxalate upon pH.

A precipitate of silver oxalate produced by this invention is much faster both in the speed of settlement and the speed of filtration than a precipitate of silver oxalate produced by a conventional method, as is specifically shown by examples to be given hereinafter. The silver oxalate precipitate produced by this invention usually has an average particle diameter of as large as about 4 to 20 micrometers, whereas a silver oxalate precipitate produced by the prior art has an average particle diameter of about 2 to 3 micrometers or below.

The silver salt and oxalate salt used as starting materials in this invention are of course different from silver oxalate obtained as the reaction product. Examples of such silver salts are silver nitrate, silver oxide and silver lactate. Silver nitrate, because of its high solubility, is preferable to water-soluble or sparingly water-soluble silver oxide and silver lactate.

The silver oxalate may, for example, be sodium oxalate, ammonium oxalate or potassium oxalate. Potassium oxalate is particularly preferred.

A combination of silver nitrate and potassium oxalate is most preferred since they are readily available and easy to handle.

The process of this invention is carried out by reacting the aforesaid starting materials in an aqueous medium while maintaining the reaction system at a pH of not more than 5, preferably 1 to 4.

Adjustment of pH may be effected by using an inorganic or organic acid. The use of an acid which reacts to form an insoluble silver salt, for example hydrochloric acid which reacts to form water-insoluble silver chloride, should be avoided. Nitric acid is most preferably used as the acid for pH adjustment.

The reaction is carried out usually at a temperature of 0° to 80° C., preferably 40° to 60° C. At these temperatures, a precipitate of silver oxalate having a relatively large particle diameter can be formed, and settling of the resulting precipitate can be quickened. At reaction temperatures above 80° C., the resulting silver oxalate tends to be colored by thermal decomposition or otherwise. The temperature of the reaction system after the formation of the precipitate has substantially been terminated is not so important.

Advantageously, the process of this invention can be performed by separately preparing an aqueous solution of the silver salt and an aqueous solution of oxalic acid and/or the oxalate, adding one of the aqueous solutions to the other and mixing them, or introducing the two aqueous solutions into another reaction vessel and mixing them in it. Most preferably, the two aqueous solutions are introduced into the other reaction vessel and mixed. At this time, there may be employed a method in which acidic water having a pH of not more than 5 is added in advance to the reaction vessel, and the two aqueous solutions are added to it. In any of these embodiments, one or both of the aqueous solutions are desirably adjusted to pH 5 or below, preferably 1 to 4, before mixing.

Preferably, the two aqueous solutions before mixing have a concentration in the range of 0.1 to 6N. More preferably, within the above concentrations, the normalities of the two aqueous solutions to be mixed are made equal to each other.

With reference to the most preferred embodiment shown above, the present invention will be further described. The speed of addition of the two aqueous solutions is determined in consideration of its relation to the stirring conditions and the concentrations of the solutions. Basically, it is important to add and stir them at such a speed of addition that the normalities of the two solutions are equal and in such a manner that great non-uniformity of concentration and localization of pH will not occur in the mixed solution. It is necessary that even partly, the pH of the mixed solution should not exceed 5. Preferably, the addition of the two aqueous solutions ends in about 1 hour although this depends upon the scale of the reaction.

In the process of this invention, the stirring is important in order to obtain complete mixing while eliminating the non-uniformity of the concentration in the solution and localization of the pH as quickly as possible. For practical purposes, the suitable stirring speed is about 10 to 500 rpm. However, after the two solutions have been added and the precipitate formed, the presence or absence of stirring is not so important.

It will be seen from the foregoing description that the preferred embodiment of the process of this invention is carried out advantageously by adding an aqueous solution of silver nitrate adjusted to pH 1–4 and an aqueous solution of potassium oxalate having almost the same normality as this (without no pH adjustment) to water adjusted to pH 1–4 with nitric acid at the same rate under well stirred conditions.

As stated above, this embodiment of the process of this invention is carried out at a pH of 1 to 4. After the reaction ends substantially and silver oxalate substantially precipitates, the pH of the reaction system is desirably adjusted to 4 or more. Thus, even after the reaction ends substantially, the silver ion dissolved in small amounts in the reaction solution may be recovered. For this purpose, a small amount of an alkali such as NaOH may be added, or potassium oxalate, for example, may be added in a slightly stoichiometrically excessive amount (5 to 10% excess).

The process of this invention can give a non-sticky precipitate of silver oxalate having a larger particle size than that formed in the prior art. Since the silver oxalate produced has a large particle size and is non-sticky, it has the following advantages.

(1) Sedimentation, filtration and water washing of the particles are easy in the filtration and washing steps.

(2) In the subsequent complexing step for catalyst preparation, the dispersibility of the particles in the solution is good and complexing is rapid.

(3) Since the precipitate is non-tacky, it is easy to handle and transport.

The following examples illustrate the present invention more specifically. Various characteristics of silver oxalate precipitate shown in Tables 1 and 2 are defined as follows:

(1) Water content: The proportion (% by weight) of water contained in the silver oxalate cake after filtration and water washing.

(2) Precipitate volume: The proportion (% by volume) of the volume of the precipitate based on the total volume of the mother liquor containing the precipitate after the precipitate was prepared and then fully left to stand.

(3) Filtration speed: The final filtration speed of the precipitate on a Buchner funnel having a suitable pore diameter selected according to the amount of the precipitate so that the thickness of the final cake becomes equal. The filter paper used is TOYO No. 2, and the degree of pressure reduction is 560 torr.

(4) Amount of washing water: The amount of water for washing the cake which is required to adjust the electric conductivity of the filtrate to 50 microohms/cm or less, expressed per unit amount of the silver oxalate precipitate.

(5) Crystal grain diameter: The average diameter of crystal grains of the silver oxalate precipitate determined by means of a scanning electron microscope.

(6) Final pH of the mother liquor: The pH of the mother liquor after the end of precipitate formation.

The characteristics (1) is a measure of the ease of handling, for example the stickiness of the precipitate.

The characteristics (3) and (4) are measures of the filtrability of the precipitate.

The characteristics (2) and (5) are measures of the size of the precipitated crystal particles.

The characteristic (6) is a measure of the amount of silver dissolved in the mother liquor. As shown in FIG. 2, if the pH is at least 4, there arises no problem of losses of silver by dissolving.

EXAMPLE 1

Thirteen liters of a nitric acid-acidified aqueous solution (1.4N) containing 3091.7 g of $AgNO_3$ and having a pH of 2.6 was prepared and heated to 60° C. Furthermore, 14.3 liters of an aqueous solution (1.4N) containing 1844.7 g of $K_2C_2O_4.H_2O$ (pH 8.6 not adjusted) was prepared and heated to 60° C. Furthermore, a mixing tank was provided which held 4.3 liters of water heated at 60° C. and adjusted to a pH of 2.5 with nitric acid. The water in the tank was stirred, and the aqueous solution of silver nitrate and aqueous solution of potassium oxalate previously prepared were fed simultaneously to the mixing tank at the same feed rate of 13 liters/hr from an opposite direction 180 degrees displaced from the tank. Specifically, silver nitrate and potassium oxalate were added in nearly equal normalities to prepare a precipitate of silver oxalate. All the aqueous silver nitrate solution was added over the course of about 60 minutes, and all the aqueous potassium oxalate, over the course of about 66 minutes. Formation of a silver oxalate precipitate ended in about 60 minutes, and in the remaining 6 minutes, a stoichiometrically excessive amount of an aqueous solution of potassium oxalate was added whereby the pH in the mixing tank was raised. Variations in the pH of the mixture in the mixing tank are shown in FIG. 1 of the accompanying drawings. The aqueous solutions fed were sufficiently stirred in the mixing tank, and the temperatures of the solutions were maintained at about 60° C. until the end of addition. The resulting precipitate was collected by filtration under reduced pressure, and washed with water. The washing was stopped when the electric conductivity of the washing water became 50 microohms/cm or less. The characteristics of the silver oxalate precipitate so obtained are shown in Table 1.

EXAMPLE 2

Example 1 was repeated except that the temperatures of the aqueous solution of silver nitrate, the aqueous solution of potassium oxalate and the water in the mixing tank were all adjusted to about 40° C., and the pH of water in the mixing tank (before mixing) was adjusted to 2. The characteristics of the resulting precipitate are shown in Table 1.

EXAMPLE 3

Example 1 was repeated except that the temperatures of the aqueous solution of silver nitrate, the aqueous solution of potassium oxalate and the water in the mixing tank were all adjusted to about 20° C., and the pH of water in the mixing tank (before mixing) was adjusted to 2. The characteristics of the resulting precipitate are shown in Table 1.

EXAMPLE 4

The temperature of the aqueous solution of silver nitrate was adjusted to about 20° C., and the temperatures of the aqueous solution of potassium oxalate and the water in the mixing tank were maintained at about 60° C. Furthermore, the pH of water in the mixing tank before mixing was adjusted to 2. The aqueous solution of potassium oxalate and the mixing tank were not kept at the initial temperatures during the mixing (so that the temperature of the mixing tank changed spontaneously, and at the end of precipitate formation, its temperature was 40°C.). Otherwise, Example 1 was repeated, and the characteristics of the resulting precipitate are shown in Table 1.

EXAMPLE 5

Example 1 was repeated except that the pH values of water in the mixing tank and the aqueous solution of silver nitrate were adjusted to 4. The characteristics of the precipitate are shown in Table 1.

COMPARATIVE EXAMPLE 1

Example 1 was repeated except that the pH values of the aqueous solution of silver nitrate and the water in the mixing tank were not adjusted (therefore, the pH of the aqueous silver nitrate solution was 5.3 and no acid was added to the water in the tank). The characteristics of the resulting precipitate are shown in Table 2.

COMPARATIVE EXAMPLE 2

Thirteen liters of an aqueous solution of silver nitrate (1.4N; pH 5.3 not adjusted) containing 3091.7 g of $AgNO_3$ was heated to about 60° C. Thirteen liters of an aqueous solution (1.54N; pH 8.6 not adjusted) containing 1844.7 g of $K_2C_2O_4 \cdot H_2O$ was heated to about 60° C. and added to the above aqueous silver nitrate solution with stirring over the course of about 30 minutes. As a result, a precipitate of silver oxalate was prepared. The precipitate was filtered and washed with water as in Example 1. The characteristics of the precipitate so obtained are shown in Table 2.

TABLE 1

| Example | 1 | 2 | 3 | 4 | 5 |
|---|---|---|---|---|---|
| Precipitate forming conditions | | | | | |
| Silver nitrate solution | | | | | |
| pH before mixing (*1) | 2.6 | 2.6 | 2.6 | 2.6 | 4.0 |
| Temperature before mixing (°C.) | 60 | 40 | 20 | 20 | 60 |
| Potassium oxalate solution | | | | | |
| pH before mixing (*2) | 8.6 | 8.6 | 8.6 | 8.6 | 8.6 |
| Temperature before mixing (°C.) | 60 | 40 | 20 | 60 | 60 |
| Water in the mixing tank | | | | | |
| pH before mixing (*1) | 2.5 | 2.0 | 2.0 | 2.0 | 4.0 |
| Temperature before mixing (°C.) | 60 | 40 | 20 | 60 | 60 |
| Characteristics of the precipitate | | | | | |
| Water content (%) | 14.8 | 17.3 | 18.5 | 14.1 | 27.3 |
| Precipitate volume (%) | 20 | 32.7 | 36.5 | 8.7 | 38.6 |
| Filtration speed (ml/min · cm$^2$) | 22.0 | 19.8 | 19.5 | 21.6 | 14.2 |
| Amount of washing water (liter/kg) | 3.1 | 3.7 | 1.8 | 1.9 | 8.4 |
| Crystal grain diameter (microns) | 15 | 10 | 10 | 15 | 15 |
| pH of the final mother liquor | 4.9 | 4.5 | 4.5 | 4.5 | 5.8 |

(*1): Adjusted with nitric acid
(*2): Not adjusted

TABLE 2

| Comparative Example | 1 | 2 |
|---|---|---|
| Precipitate forming conditions | | |
| Silver nitrate solution pH before mixing (*3) | 5.3 | 5.3 |
| Temperature before mixing (°C.) | 60 | 60 |
| Potassium oxalate solution pH before mixing (*3) | 8.6 | 8.6 |
| Temperature before mixing (°C.) | 60 | 60 |
| Water in the mixing tank pH before mixing (*3) | 5.8 | — |
| Temperature before mixing (°C.) | 60 | — |
| Characteristics of the precipitate | | |
| Water content (%) | 19.7 | 20.0 |
| Precipitate volume (%) | 41.4 | 40.0 |
| Filtration speed (ml/min · cm$^2$) | 2.0 | 2.1 |
| Amount of washing water (liter/kg) | 10.3 | 11.5 |
| Crystal grain diameter (microns) | 3 | 2 |
| pH of the final mother liquor | 6.1 | 6.9 |

(*3) Not adjusted

EXAMPLE 6

129.3 g (78.9 g as silver) of the silver oxalate cake having a water content of 14.1%, prepared in Example 4, was taken, and added to an aqueous amine solution composed of 39.5 g of ethylenediamine, 10.8 g of 1,3-diaminopropane and 50.0 g of water to prepare a solution of silver oxalate/amine complex. The solution was fully stirred and the speed of addition was controlled so that the temperature of the solution did not rise beyond 35° C. owing to the heat of complexing. The silver oxalate precipitate well dispersed in the aqueous amine solution, and the complexing reaction proceeded easily. The time required until a solution of the complex formed was 37 minutes.

COMPARATIVE EXAMPLE 3

A solution of silver oxalate/amine complex was prepared in the same way as in Example 6 except that 138.9 g (78.9 g as silver which was the same as the amount of silver used in Example 6) of the silver oxalate cake having a water content of 20.0%, prepared in Comparative Example 2, was used. The silver oxalate precipitate adhered in masses to the lower part of the complexing reaction vessel and the complexing reaction was difficult of proceeding. The time required until the preparation of a solution of the complex ended was 84 minutes.

What is claimed is:

1. A process for producing silver oxalate, which comprises reacting
    (a) one member selected from the group consisting of oxalic acid and oxalic acid salts as one reactant, with
    (b) a silver salt as the other reactant, at a pH of not more than 5 in an aqueous medium thereby to precipitate silver oxalate.

2. The process of claim 1 wherein the reaction is carried out at a temperature in the range of 0° to 80° C.

3. The process of claim 1 wherein the reaction is carried out at a pH of not more than 4.

4. The process of claim 1 wherein the reaction is carried out at a pH of not more than 4, and after silver oxalate has substantially precipitated, the pH of the reaction system is adjusted to a value higher than 4.

5. The process of claim 1 wherein the oxalate as one reactant is potassium oxalate.

6. The process of claim 1 wherein the silver salt as the other reactant is silver nitrate.

7. The process of claim 1 wherein the pH is adjusted to not more than 5 with nitric acid.

8. The process of claim 1 wherein the reactants are prepared each in the form of an aqueous solution before mixing them.

9. The process of claim 8 wherein the concentration of the aqueous solution of the silver salt as reactant is 0.1 to 6N.

10. The process of claim 8 wherein the concentration of the aqueous solution of oxalic acid or the oxalate as reactant is 0.1 to 6.

11. The process of claim 1 wherein an aqueous solution of silver nitrate adjusted to pH 1-4 and an aqueous solution of potassium oxalate having nearly the same normality as the first-mentioned aqueous solution are added at nearly the same speed to stirred water adjusted to pH 1-4, and after the two aqueous solutions have been added, a stoichiometrically excessive amount of an aqueous solution of potassium oxalate is further added to raise the pH to more than 4.

* * * * *